United States Patent [19]

Auner

[11] Patent Number: 5,880,306
[45] Date of Patent: Mar. 9, 1999

[54] SILYL CATIONS AND PROCESS FOR MAKING THEM

[75] Inventor: Norbert Auner, Berlin, Germany

[73] Assignee: Dow Corning, Ltd., Wales, United Kingdom

[21] Appl. No.: 920,152

[22] Filed: Aug. 26, 1997

[30] Foreign Application Priority Data

Aug. 30, 1996 [GB] United Kingdom .................... 9618215

[51] Int. Cl.$^6$ ....................................................... C09F 7/08
[52] U.S. Cl. ........................... 556/465; 556/406; 556/487; 556/489
[58] Field of Search ..................................... 556/465, 487, 556/489, 406

[56] References Cited

U.S. PATENT DOCUMENTS 5,266,670  11/1993  Nakos et al. .......................... 556/489 X

OTHER PUBLICATIONS

Chemical Reviews, vol. 95, pp. 1191–1201, (1995).
Organomettallics, vol. 13, pp. 2430–2443, (1994).
Science, vol. 260, pp. 1917–1918, (1993).
Angew. Chem., vol. 105, pp. 1558–1561, (1993).
Z. Naturforsch, vol. 49b, pp. 1743–1754, (1994).
Chem. Eng. News, Jun. 28, 1993, p. 7.
Journal of American Chemical Society, vol. 113, pp. 8570–8571, (1991).

*Primary Examiner*—Paul F. Shaver
*Attorney, Agent, or Firm*—James E. Bittell

[57] ABSTRACT

Silyl cation of the formula $Si^+R_2R'$ wherein R denotes a hydrogen, a hydrocarbon or fluorine and R' denotes a norbornyl or cyclopentenyl containing substituent is free of co-ordination with a solvent and is stable at a temperature of upto at least 40°C. Also disclosed is a compound consisting of the cation and a borate or carborane anion, a composition comprising the cation and a solvent and a process for making the cation.

17 Claims, No Drawings

SILYL CATIONS AND PROCESS FOR MAKING THEM

This invention relates to silyl cations and a process for making them.

Silyl cations are known and have been described, for example, in Chemical Reviews 1995, Volume 95, pages 1191 to 1201 together with processes for making them.

Conventional processes for the formation of silyl cations are based on an adaptation of the intermolecular hydride-transfer reaction of Bartlett-Condon-Schneider which involves the reaction of a carbocation with a silicon hydride to yield a silyl cation and a hydrocarbon.

In Organometallics 1994, Volume 13, pages 2430 to 2443 a reaction mechanism has been described as:

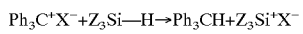

$$Ph_3C^+X^- + Z_3Si\text{—}H \rightarrow Ph_3CH + Z_3Si^+X^-$$

wherein Ph denotes phenyl, Z is exemplified by methyl, ethyl, isopropyl, isobutyl, hexyl, phenyl and trimethylsilyl and X is exemplified by hydrogen, tetrakis (pentafluorophenyl)borate and $ClO_4$.

Products resulting from a mechanism as described above carried out in the presence of toluene with triethylsilyl and triphenylmethyl(pentafluorophenyl)borate) have been reported in Science 1993, Volume 260, pages 1917 to 1918 as having the crystal structure of triethylsilylium tetrakis (pentafluorophenyl)borate which incorporated a stable silyl cation with no coordination to the anion and distant coordination to the solvent.

Schleyer and co-workers in Angew. Chem. 1993, Volume 105, pages 1558 to 1561 have demonstrated by ab initio calculations that the silyl cations as prepared in the previous two articles are actually $[Z_3Si\text{-toluene}]^-\sigma$ complex-arenium ions in which the positive charge is substantially delocalised to the aromatic ring of the solvent.

There has been a continued search for silyl cations which are stable without the need for coordination to the solvent.

According to the invention there is provided a silyl cation of the formula $Si+R_2R'$ wherein R denotes a hydrogen, a hydrocarbon or fluorine and R' denotes a norbornyl or cyclopentenyl containing substituent.

Each substituent R may be the same or different and denotes a hydrogen, a hydrocarbon or fluorine. Preferably each R is a hydrogen, an alkyl or aryl group, and more preferably a hydrogen, a methyl or phenyl group with a methyl group the most preferred substituent. R' represents a norbornyl or cyclopentenyl containing substituent. Preferably R' is such that the silyl cation has one of the following formulae:

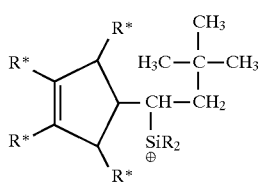

(I)

or

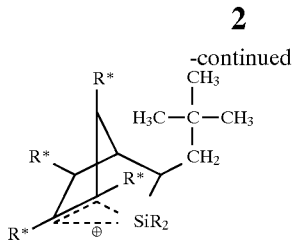

(II)

(III)

which is equivalent to wherein $R^+$ denotes a hydrogen or an alkyl group having up to 4 carbon atoms and preferably a hydrogen or a methyl group and most preferably a hydrogen.

Silyl cations are usually countered by anions to form compounds according to a second aspect of the invention. Anions suitable as counter ions to the silyl cations may be derived from borates or carboranes. Preferably the anion is an arylborate or closocarborane ion, more preferably tetrakis (pentafluorophenyl)borate or tetrakis[bis(3,5-trifluoromethylphenyl)]borate with tetrakis (pentafluorophenyl)borate most preferred.

The silyl cation may be present in a composition which also comprises solvent. The solvent is believed to solubilise the cation. Suitable solvents include aromatic solvents, polar solvents and mixtures of two or more of either or both types of these. Examples of suitable solvents are dichloromethane, 1,2-dichloroethane, ethers, sulpholanes and nitrites e.g. acetonitrile. The solvent is preferably aromatic, more preferably benzene or toluene and most preferably toluene.

According to another aspect of the invention there is provided a process for making a silyl cation according to the first aspect of the invention which comprises the reaction of a silane of the formula $HSiR_2R''$ wherein R is as defined as above and R'' denotes a cyclopentenyl containing substituent, with a borate or carborane.

In the silane $HSiR_2R''$, the substituent R'' is preferably

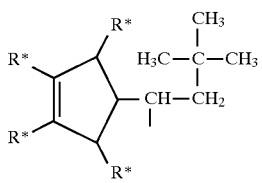

(III)

where R* is as defined above. Silanes suitable for use in the process according to the invention may be prepared, for example, according to the method described in detail in Z. Naturforsch 1994, Volume 49b, pages 1743 to 1754.

Suitable borates and carboranes may be salts of the formula $A^+B^-$ wherein $A^+$ is derived from borates or carboranes, preferably arylborates or closocarboranes and more preferably from tetrakis(pentafluorophenyl)borate or tetrakis[bis (3,5-trifloromethylphenyl)]borate and $B^-$ is a hydrocarbyl group for example a phenyl substituted alkyl group e.g. triphenylmethyl group. Examples of suitable borates are triphenylmethyltetrakis(pentafluorophenyl) borate and triphenylmethyltetrakis[bis(3,5-trifluoromethylphenyl)]borate.

The process according to the invention may be carried out in the presence of a solvent. Suitable solvents include aromatic solvents, polar solvents or mixtures of two or more of either or both types of these. Examples of suitable solvents are dichloromethane, 1,2-dichloroethane, ethers, sulpholanes and nitrites e.g. acetonitrile. The solvent is preferably aromatic more preferably benzene or toluene and most preferably toluene. Preferably the process is carried out in an inert atmosphere for example nitrogen or argon.

Suitably the process is carried out by introducing the reagents i.e. the silane and borate or carborane into a reaction vessel optionally in the presence of a solvent and preferably agitating the mixture. The reaction temperature is not critical and may vary from below ambient to elevated temperatures, for example, −100° to 50° C., more preferably −30° to 30° C. and most preferably at around 20° C. After the reaction period, the silyl cation may be retained in the reaction mixture or recovered from the reaction mixture for example by separation and/or solvent evaporation.

Silyl cations according to the invention are free of co-ordination with a solvent and are found to be stable at a temperature of upto at least 40° C.

Silyl cations according to the invention are usefully employed in a variety of applications, for example, the formation of silicones as referred to on page 7 of Chemical Engineering News of 28th June 1993.

The following examples illustrate the invention:

EXAMPLE

A.

Preparation of 2-Chloro-3-(3-cyclopentenyl)-2,5,5-trimethyl-2-silahexane

2-Chloro-3-(3-cyclopentenyl)-2,5,5-trimethyl-2-silahexane was prepared according to the method of Auner and Steinberger as found in Z. Naturforsch. 1994, Volume 49b, pages 1743 to 1754.

B.

Preparation of 3-(3-Cyclopentenyl)-2,5,5-trimethyl-2-silahexane

To 600 mg (15.80 mmol) of lithium aluminium hydride cooled to a temperature of 0° C., 3.87 g (15.80 mmol) of 2-chloro-3-(3-cyclopentenyl)-2,5,5-trimethyl-2-silahexane (as described in A above) was added dropwise. The mixture was refluxed for 3 hours and the excess lithium aluminum hydride removed from the mixture by filtration. The mixture was distilled and 2.66 g of a colourless liquid (boiling point of 67° C. at 102 mbar) was isolated which is a yield of 80%. The liquid was characterised by $^{29}$Si NMR in CDCl$_3$ and was shown to be 3-(3-cyclopentenyl)-2,5,5-trimethyl-2-silahexane with a chemical shift of δ=−10.32 ppm.

C.

Preparation of Triphenylmethyltetrakis (pentafluorophenyl)borate

The synthesis of triphenylmethyltetrakis (pentafluorophenyl)borate was according to the method of Chien et al. as described in the Journal of American Chemical Society 1991, Volume 113, pages 8570 to 8571.

D.

Preparation of Dimethyl-neopentyl-silanorbornyl-tetrakis(pentafluorophenyl)borate To 2.46 g (2.62 mmol) of triphenylmethyltetrakis (pentafluorophenyl)borate (made according to C above) at room temperature, under an argon blanket in a flame-dried NMR tube, 2.5 ml of d$_8$-toluene and 551 mg (2.62 mmol) of 3-(3-cyclopentenyl)-2,5,5-trimethyl-2-silahexane (B) were added via a syringe and the resulting mixture was agitated. The mixture separated into two layers and the top layer was removed and characterised by $^{29}$Si (INEPT)—NMR in d$_8$ toluene. The top layer was shown to contain dimethyl-neopentyl-silanorbornyl-tetrakis-(pentafluorophenyl)-borate with a chemical shift of 87.7 ppm, which confirms the presence of a silyl cation without any coordination with the toluene solvent.

E.

Preparation of Exo/Endo-3-Neopentyl-2,2-diphenyl-2-silabicyclo[2.2.1]heptane

To 10–15 mg (10–16 μmol) of triphenylmethyltetrakis (pentafluorophenyl)borate (made according to C above) at room temperature, under a nitrogen blanket in a flame-dried round-bottomed flask, 20 ml toluene was added to form a brownish coloured solution. 906 mg (2.70 mmol) of 2-(3-cyclopentenyl)-4,4-dimethyl-1,1-diphenyl-silapentane was slowly added via a syringe to the borate solution. The mixture was left overnight and then the toluene was removed from the mixture under high vacuum. The resulting residue was dissolved in 70 ml Hexane. The solution was filtered/decanted and then crystallised to give a powdery substance with a product yield of 852 mg (94%). The product was shown by $^1$H, $^{13}$C and $^{29}$Si NMR and elemental analysis to be Exo/Endo-3-Neopentyl-2,2-diphenyl-2-silabicyclo[2.2.1]heptane $^{29}$Si NMR (CDCl$_3$) δ=10.99 for the Exo variant, $^{29}$Si NMR δ=−0.36 for the Endo variant.

F.

Preparation of Endo/Exo-3-Neopentyl-2-silabicyclo [2.2.1]-silaheptane

To a borate solution as made according to E above, 1.50 g (8.22 mmol) of 2-(3-cyclopentenyl)-4,4-dimethyl-silapentane was slowly added. After 1 hour at room temperature, 20 ml hexane was added and the solution was then filtered and the solvent removed under high vacuum. Fractional distillation of the product gave a product yield of 1.27 g (85% yield). The product was shown by $^1$H, $^{13}$C and $^{29}$Si NMR and elemental analysis to be Exo/Endo-3-Neopentyl-2-silabicyclo [2.2.1]-silaheptane. $^{29}$Si NMR (CDCl$_3$) δ=−10.23 for the Exo variant, δ=−16.03 for the Endo variant.

That which is claimed is:

1. A silyl cation of the formula Si$^+$R$_2$R' wherein R is selected from the group consisting of hydrogen, a hydrocarbon and fluorine and R' is selected from the group consisting of norbornyl containing substituents and cyclopentenyl containing substituents.

2. A silyl cation according to claim 1 wherein R is selected from the group consisting of hydrogen, a methyl group and a phenyl group.

3. A silyl cation according to claim 1 selected from the formulae consisting of

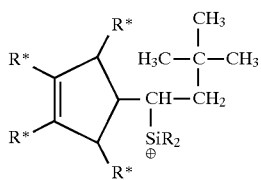

(I)

and

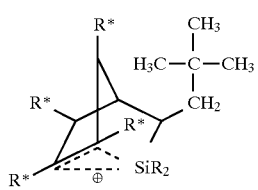

(II)

wherein R* is selected from the group consisting of hydrogen and alkyl groups having up to 4 carbon atoms and R is selected from the group consisting of hydrogen, a hydrocarbon and fluorine.

4. A silyl cation according to claim 3 wherein R is selected from the group consisting of hydrogen, a methyl group and a phenyl group.

5. A compound consisting of
   (a) a silyl cation of the formula $Si^+R_2R'$ wherein R is selected from the group consisting of hydrogen, a hydrocarbon and fluorine and R' is selected from the group consisting of norbornyl containing substituents and cyclopentenyl containing substituents and
   (b) an anion selected from the group consisting of borate anions and carborane anions.

6. A compound according to claim 5 wherein the silyl cation has the formula selected from the group consisting of

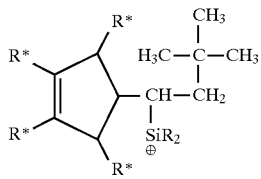

(I)

and

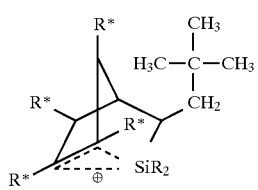

(II)

wherein R* is selected from the group consisting of hydrogen and alkyl groups having up to 4 carbon atoms and R is selected from the group consisting of hydrogen, a methyl group and a phenyl group.

7. A compound according to claim 5 wherein the anion is selected from the group consisting of tetrakis(pentafluorophenyl)borate and tetrakis[bis(3,5-trifluoromethyl)phenyl]borate.

8. A composition comprising
   (a) a silyl cation of the formula $Si^+R_2R'$ wherein R is selected from the group consisting of hydrogen, a hydrocarbon and fluorine and R' is selected from the group consisting of norbornyl containing substituents and cyclopentenyl containing substituents and
   (b) a solvent.

9. A composition according to claim 8 wherein the silyl cation has the formula selected from the group consisting of:

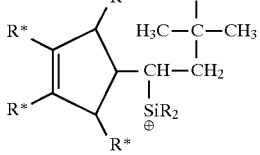

(I)

and

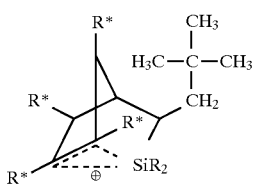

(II)

wherein R* is selected from the group consisting of hydrogen and alkyl groups having up to 4 carbon atoms and R is selected from the group consisting hydrogen, a methyl group and a phenyl group.

10. A composition according to claim 8 wherein the solvent is an aromatic solvent.

11. A composition according to claim 8 wherein the solvent is selected from the group consisting of benzene and toluene.

12. A process for making a silyl cation of the formula $Si^+R_2R'$ which comprises the step of reacting a silane of the formula $HSiR_2R''$ with a compound selected from the group consisting of borates and carboranes wherein R is selected from the group consisting of hydrogen, a hydrocarbon and fluorine, R' is selected from the group consisting of norbornyl containing substituents and cyclopentenyl containing substituents and R" denotes cyclopentenyl containing substituents.

13. A process according to claim 12 wherein each R is independently selected from the group consisting of hydrogen, a methyl group and a phenyl group.

14. A process according to claim 12 wherein R" denotes

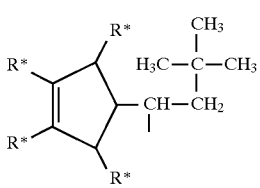

(III)

in which R* is selected from the group consisting of hydrogen and alkyl groups having up to 4 carbon atoms.

15. A process according to claim 12 wherein the silane is reacted with a borate compound selected from the group consisting of triphenylmethyltetrakis(pentafluorophenyl)borate and triphenylmethyltetrakis[bis (3,5-trifluoromethyl)-phenyl]borate.

16. A process according to claim 12 wherein the reaction is carried out in the presence of a solvent.

17. A process according to claim 16 wherein the solvent is selected from the group consisting of toluene and benzene.

* * * * *